United States Patent [19]

Fancher

[11] 3,975,419

[45] Aug. 17, 1976

[54] 2,4-DICHLOROPHENOXYACETYL THIOLCARBAMATE HYDRAZINES

[75] Inventor: Llewellyn W. Fancher, Orinda, Calif.

[73] Assignee: Stauffer Chemical Company, Westport, Conn.

[22] Filed: Dec. 10, 1975

[21] Appl. No.: 639,314

[52] U.S. Cl............................. 260/455 A; 71/100; 71/108; 260/471 C
[51] Int. Cl.².................................... C07C 155/02
[58] Field of Search................. 260/455 A

[56] References Cited
UNITED STATES PATENTS

| | | | |
|---|---|---|---|
| 2,673,159 | 3/1954 | Beaver............................ | 260/455 A |
| 3,287,099 | 11/1966 | D'Amico et al. ............... | 260/455 A |
| 3,419,659 | 12/1968 | Catino et al. ................... | 260/455 A |
| 3,496,153 | 2/1970 | Halasa ............................ | 260/455 A |

FOREIGN PATENTS OR APPLICATIONS

| 3,912,925 | 7/1959 | Japan.............................. | 260/455 A |

Primary Examiner—Lewis Gotts
Assistant Examiner—D. R. Phillips
Attorney, Agent, or Firm—Edith A. Rice

[57] ABSTRACT

Novel compounds of the general formula:

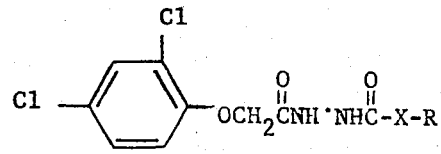

wherein X is oxygen or sulfur; and R is selected from the group consisting of alkyl containing 1 through 8 carbon atoms, halosubstituted alkyl containing 1 through 8 carbon atoms, phenyl, benzyl, and halosubstituted phenyl are herbicidally active.

10 Claims, No Drawings

2,4-DICHLOROPHENOXYACETYL THIOLCARBAMATE HYDRAZINES

DESCRIPTION OF THE INVENTION

This invention is directed to herbicidally active 2,4-dichlorophenoxyacetyl carbamate and thiolcarbamate hydrazides and to their use as herbicides. The compounds of the present invention are represented by the general structural formula

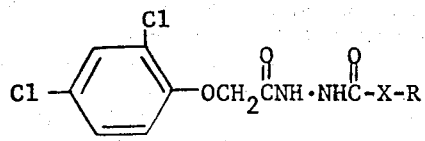

wherein X is oxygen or sulfur; and R is selected from the group consisting of alkyl containing 1 through 8 carbon atoms, halosubstituted alkyl containing 1 through 8 carbon atoms, phenyl, benzyl and halosubstituted phenyl.

The compounds of this invention can be prepared by reacting 2,4-dichlorophenoxyacetylhydrazide with the appropriate chloroformate or chlorothiolformate in the presence of a tertiary amine base. This reaction is represented by the following equation:

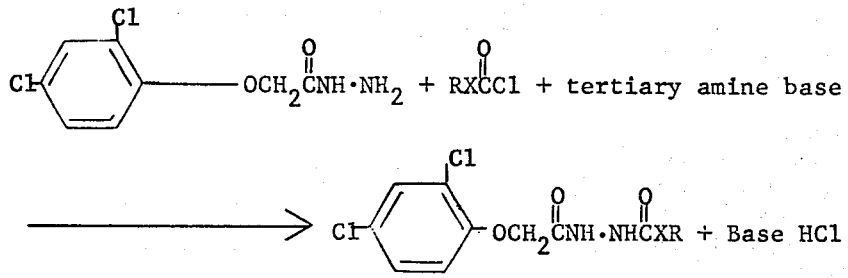

wherein X and R are as defined above.

The reaction is carried out in the presence of an unreactive solvent, for example, water soluble solvents such as dimethylformamide, dimethyl sulfoxide, tetrahydrofuran, and dioxane, and water insoluble solvents such as trichloromethane, dichloromethane, and the like. Illustrative examples of tertiary amine bases that can be used in this reaction are pyridine, substituted pyridines, and trialkyl amines. Other tertiary amine bases are also suitable. The temperature at which the reaction takes place will generally be in the range of about 0°C to about 30°C.

The following examples illustrate the preparation of typical compounds of this invention and demonstrate the herbicidal activity thereof.

EXAMPLE I

This example describes the preparation of 1-(2',4'-dichlorophenoxyacetyl)-2-carboethoxyhydrazide:

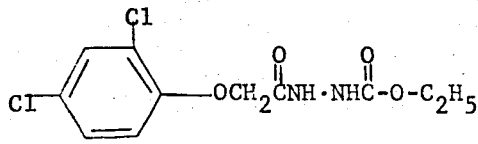

A slurry was formed containing 4.3 grams (0.02 mole) of 2,4-dichlorophenoxyacetylhydrazide slurried in 25 mls of dimethylformamide. To this slurry was added 4.0 g (0.05 mole) of pyridine and the mixture was cooled to 5°C. The mixture was stirred and 3.3 g (0.03 mole) ethylchloroformate was added with cooling to maintain the temperature below 15°C. The resulting clear solution was allowed to stand overnight at ambient temperature without stirring. The solution was then poured into 200 cc of cold water to precipitate the solid product which was isolated by filtration, washed with cold water and dried at 50°C. The white solid product weighed 6.2 g (theory equals 6.1 g) and had a melting point of 152°–155°C. The structure of the product was confirmed by I.R.

EXAMPLE II

This example describes the preparation of 1-(2',4'-dichlorophenoxyacetyl)-2-carbo-n-propylthiolhydrazide:

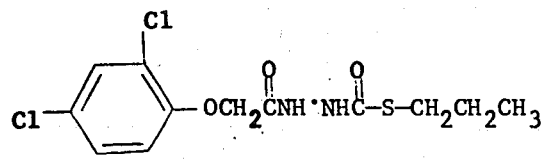

A slurry was formed containing 4.7 g (0.02 mole) of 2,4-dichlorophenoxyacetylhydrazide slurried in 25 mls of dimethylformamide. To this slurry was added 4.0 g (0.05 mole) of pyridine and the mixture was cooled to 5°C. The mixture was stirred and 3.5 g (0.025 mole) of n-propylchlorothiolformate was added with cooling to maintain the temperature below 15°C. The resulting clear solution was stirred at ambient temperature for one and a half hours, allowed to stand overnight and then stirred for an additional 0.5 hours. The mixture was then poured into 200 mls of cold water to precipitate the solid product which was isolated by filtering and then washed with cold water. The product was dried at 40°C for two hours then recrystalized from benzene to obtain a white solid weighing 5.1 g (theory equal 6.74 g). The product had a melting point of 123°–126°C. The structure was confirmed by I.R. and M.S.

Other compounds were compared in an analogous maner from 2,4-dichlorophenoxyacetylhydrazide and the appropriate chloroformate or chlorothiolformate. The following is a table of compounds representative of those embodied in the present invention. Compound numbers have been assigned to them and are used for identification throughout the balance of the specification.

TABLE I

| Compound Number | X | R | Melting Point (°C) |
|---|---|---|---|
| 1 | O | C$_2$H$_5$ | 152–155 |
| 2 | S | C$_2$H$_5$ | 141–146 |
| 3 | S | i-C$_3$H$_7$ | 115–119 |
| 4 | O | CH$_3$ | 154–158 |
| 5 | O | CH$_2$CH$_2$Cl | 156–167 |
| 6 | O | n-C$_3$H$_7$ | 120–124 |
| 7 | O | n-C$_4$H$_9$ | 124–126.5 |
| 8 | O | n-C$_6$H$_{13}$ | 94–99 |
| 9 | S | n-C$_3$H$_7$ | 123–126 |
| 10 | S | n-C$_4$H$_9$ | 122–125 |
| 11 | S | —C$_6$H$_4$—Cl | 143–152 |
| 12 | O | i-C$_4$H$_9$ | 106–109 |
| 13 | S | i-C$_4$H$_9$ | 139–144 |
| 14 | S | sec-C$_4$H$_9$ | 84–88 |
| 15 | S | n-C$_8$H$_{17}$ | 112–116 |
| 16 | S | —CH$_2$—C$_6$H$_5$ | 125–129 |
| 17 | O | —C$_6$H$_5$ | 136–140 |

Herbicidal Screening Tests

As previously mentioned, the novel compounds herein described are phytotoxic compounds which are useful and valuable in controlling various plant species. Compounds of this invention are tested as herbicides in the following manner.

Pre-emergence herbicide screening test

Using an analytical balance, 20 mg of the compound to be tested is weighed out on a piece of glassine weighing paper. The paper and compound are placed in a 30 ml widemouth bottle and 3 ml of acetone containing 1% Tween 20, a polyoxyethylene derivative of sorbitan monolaurate, is added to dissolve the compound. If the material is not soluble in acetone, another solvent such as water, alcohol or dimethylformamide (DMF) is used instead. When DMF is used, only 0.5 ml or less is used to dissolve the compound and then another solvent is used to make the volume up to 3 ml. The 3 ml of solution is sprayed uniformly on the soil contained in a small Styrofoam flat one day after planting weed seeds in the flat of soil. A No. 152 DeVilbiss atomizer is used to apply the spray using compressed air at a pressure of 5 lb/sq. inch. The rate of application is 8 lb/acre and the spray volume is 143 gal./acre.

On the day preceding treatment, the Styrofoam flat, which is 7 inches long, 5 inches wide and 2.75 inches deep, is filled to a depth of 2 inches with loamy sand soil. Seeds of seven different weed species are planted in individual rows using one species per row across the width of the flat. The seeds are covered with soil so that they are planted at a depth of 0.5 inch. The seeds used are hairy crabgrass (*Digitaria Sanguinalis*), yellow foxtail (*Seteria glauca*), watergrass (*Echinochloa crusgalli*), red oat (*Avena sativa*), redroot pigweed (*Amaranthus retroflexus*), Indian mustard (*Brassica juncea*), and curly dock (*Rumex crispus*). Ample seeds are planted to give about 20 to 50 seedlings per row after emergence depending on the size of the plants.

After treatment, the flats are placed in the greenhouse at a temperature of 70° to 85°F and watered by sprinkling. Two weeks after treatment the degree of injury or control is determined by comparison with untreated check plants of the same age. The injury rate from 0 to 100% is recorded for each species as percent control with 0% representing no injury and 100% representing complete kill.

Post-emergence herbicide screening test

Seeds of six plant species, including hairy crabgrass, watergrass, red oat, mustard, curly dock and pinto beans (*Phaseolus vulgaris*) are planted in the Styrofoam flats as described above for pre-emergence screening. The flats are placed in the greenhouse at 70° to 85°F. and watered daily with a sprinkler. About 10 to 14 days after planting when the primary leaves of the bean plants are almost fully expanded and the first trifoliate leaves are just starting to form, the plants are sprayed. The spray is prepared by weighing out 20 mg of the test compound, dissolving it in 5 ml of acetone containing 1% Tween 20 and then adding 5 ml of water. The solution is sprayed on the foliage using a No. 152 DeVilbiss atomizer at an air pressure of 5 lb/sq. inch. The spray concentration is 0.2% and the rate is 8 lb/acre. The spray volume is 476 gal/acre.

Injury ratings are recorded 14 days after treatment. The rating system is the same as described above for the pre-emergence test.

The results of these tests are shown in Table II.

TABLE II

| Compound Number | Percent control* at 8 lb/acre | |
|---|---|---|
| | Pre-emergence | Post-emergence |
| 1 | 86 | 86 |
| 2 | 66 | 88 |
| 3 | 79 | 88 |
| 4 | 92 | 82 |
| 5 | 82 | 73 |
| 6 | 90 | 87 |
| 7 | 76 | 88 |
| 8 | 78 | 87 |
| 9 | 61 | 89 |
| 10 | 80 | 88 |
| 11 | 68 | 70 |
| 12 | 79 | 86 |
| 13 | 63 | 87 |
| 14 | 79 | 86 |
| 15 | 81 | 71 |
| 16 | 59 | 83 |
| 17 | 62 | 78 |

*Average for seven plant species in the pre-emergence test and for six plant species in the post-emergence test.

The compounds of the present invention can be used in any convenient form. Thus, the compounds can be made into emulsifiable liquids, emulsifiable concentrates, liquid, wettable powder, powders, granular or any other convenient form, and applied to the soil to control the undesired vegetation.

What is claimed is:

1. A compound having the general structural formula:

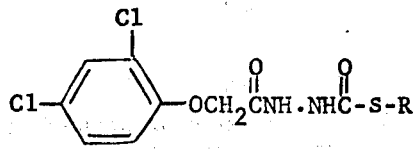

wherein R is selected from the group consisting of alkyl contaiing 1 through 8 carbon atoms, halosubstituted alkyl containing 1 through 8 carbon atoms, phenyl, benzyl and halosubstituted phenyl.

2. The compound as set forth in claim 1 wherein R is C$_2$H$_5$.

3. The compound as set forth in claim 1 wherein R is i-C$_3$H$_7$.

4. The compound as set forth in claim 1 wherein R is n-C$_3$H$_7$.

5. The compound as set forth in claim 1 wherein R is n-C$_4$H$_9$.

6. The compound as set forth in claim 1 wherein R is

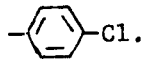

7. The compound as set forth in claim 1 wherein R is i-C$_4$H$_9$.

8. The compound as set forth in claim 1 wherein R is sec-C$_4$H$_9$.

9. The compound as set forth in claim 1 wherein R is n-C$_8$H$_{17}$.

10. The compound as set forth in claim 1 wherein R is

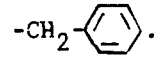

* * * * *